(12) United States Patent
Taylor

(10) Patent No.: US 8,927,272 B2
(45) Date of Patent: Jan. 6, 2015

(54) METHOD AND DEVICE FOR PERFORMING BIOPSIES ON A VESICULAR OBJECT

(71) Applicant: Paul J. Taylor, Bozeman, MT (US)

(72) Inventor: Paul J. Taylor, Bozeman, MT (US)

( * ) Notice: Subject to any disclaimer, the term of this patent is extended or adjusted under 35 U.S.C. 154(b) by 96 days.

(21) Appl. No.: 13/986,029

(22) Filed: Mar. 25, 2013

(65) Prior Publication Data
US 2014/0287493 A1    Sep. 25, 2014

(51) Int. Cl.
*C12N 5/073*    (2010.01)
*B01L 3/02*    (2006.01)

(52) U.S. Cl.
CPC ............ *C12N 5/0604* (2013.01); *B01L 3/021* (2013.01)
USPC ............... 435/325; 435/309.1; 435/287.3

(58) Field of Classification Search
None
See application file for complete search history.

(56) References Cited

U.S. PATENT DOCUMENTS

| 8,357,103 B2 | 1/2013 | Mark |
| 8,376,957 B2 | 2/2013 | Hibner |
| 8,394,033 B2 | 3/2013 | DiCarlo |

*Primary Examiner* — Ruth Davis
*Assistant Examiner* — Emily Cordas

(57) ABSTRACT

A method for removing material from a vesicular object by securing the object, penetrating the object with a pipette, such pipette having a sealed distal tip and an aperture, advancing said pipette into the object in such a manner as to place the aperture directly adjacent to the material to be removed from the object, applying vacuum inside the pipette thereby drawing the material to be removed from the object into the pipette, and removing the pipette from the object in such a manner as to cut or otherwise separate the material in the pipette from the object thereby leaving the material removed from the object in the pipette while leaving the object undamaged.

1 Claim, 2 Drawing Sheets

DETAIL A

DETAIL B

METHOD AND DEVICE FOR PERFORMING BIOPSIES ON A VESICULAR OBJECT

CROSS-REFERENCE TO RELATED APPLICATIONS

This application claims the benefit of PPA Ser. No. 61/686,025 filed Mar. 28, 2012 by the present inventor, which is incorporated by reference.

FEDERALLY SPONSORED RESEARCH

This invention was not made under a government contract and the government has no rights in it.

SEQUENCE LISTING OR PROGRAM

Not applicable.

BACKGROUND—PRIOR ART

The following is a tabulation of some prior art that presently appears relevant:

U.S. Patents

| Pat. No. | ISSUE DATE | PATENTEE |
| --- | --- | --- |
| 8,394,033 | July 2006 | DiCarlo |
| 8,376,957 | February 2013 | Hibner |
| 20060200040 | September 2006 | Weikel |
| 8,357,103 | January 2013 | Mark |

BACKGROUND

The present method and device relates to a method and device for removing tissue or other cellular material (cellular material) from a vesicular object having a size typically in the neighborhood of 100-300 microns. This method and device has particular application for removing cellular material from mammalian embryos at the hatched blastocyst stage of development. This has not been possible with previous devices which have been mostly designed for biopsies of a much larger nature.

Removing material from the hatched blastocyst has been difficult because the blastocysts are spherical vesicular structures consisting of a thin double layer of living cells surrounding a relatively large central cavity that is filled with an aqueous fluid. The difficulty, and the failure of the prior art, arises because of the physical characteristics of the envelope of these living cells which is flimsy but resistant to puncture. For example, attempts to puncture a hatched blastocyst often simply compress the envelope of the embryo without puncturing it. With the present device there is no compression at all.

ADVANTAGES OF THE EMBODIMENT

The present method and device overcomes the above-described difficulties by providing a method and device wherein the object is firmly held, for example, by using a vacuum as described in application Ser. No. 13/374,195, the object is then pierced by the probe. An aperture, or biopsy port, on one side of the probe is then aligned with the material to be removed. A vacuum applied to the interior of the probe draws the cellular material into the probe itself for subsequent removal from the vesicular object.

An additional advantage lies in fact the present method and device leaves the object unharmed after the biopsy. As an example only, the puncture wound made in the surface of an expanding or hatched blastocyst by the biopsy probe will involve less than 0.01% of the surface. In a living embryo (blastocyst), this wound is surrounded by rapidly dividing cells on all sides. As soon as the probe is withdrawn, the wound closes tightly enough to prevent leakage of fluid into or out of the blastocoel space and will heal closed completely within a few hours.

A yet additional advantage is that smaller biopsy probes, down to 4 um outside diameter (OD) near the tip end, with biopsy ports at least as small as 2 um diameter, can be made at present. This is small enough to be used on certain large individual cells, with the possibility to remove and capture cellular components such as the nucleus or mitochondria. Smaller probes, and biopsy ports are possible.

SUMMARY, CONCLUSION, RAMIFICATIONS, AND SCOPE

The above-described method and device punctures and allows removal of cellular material from a very specific location on a vesicular object. For example, an identifiable portion of the surface of a hatched blastocyst is the Inner Cell Mass, consisting of embryonic stem cells. This device has the potential to harvest embryonic stem cells without serious damage to the embryo.

BRIEF DESCRIPTION OF THE DRAWINGS

In order that the method and device may be clearly understood and readily carried into effect, a preferred embodiment of the invention will now be described, by way of example only, with reference to the accompanying drawings wherein.

REFERENCE NUMERALS

Figure 1:
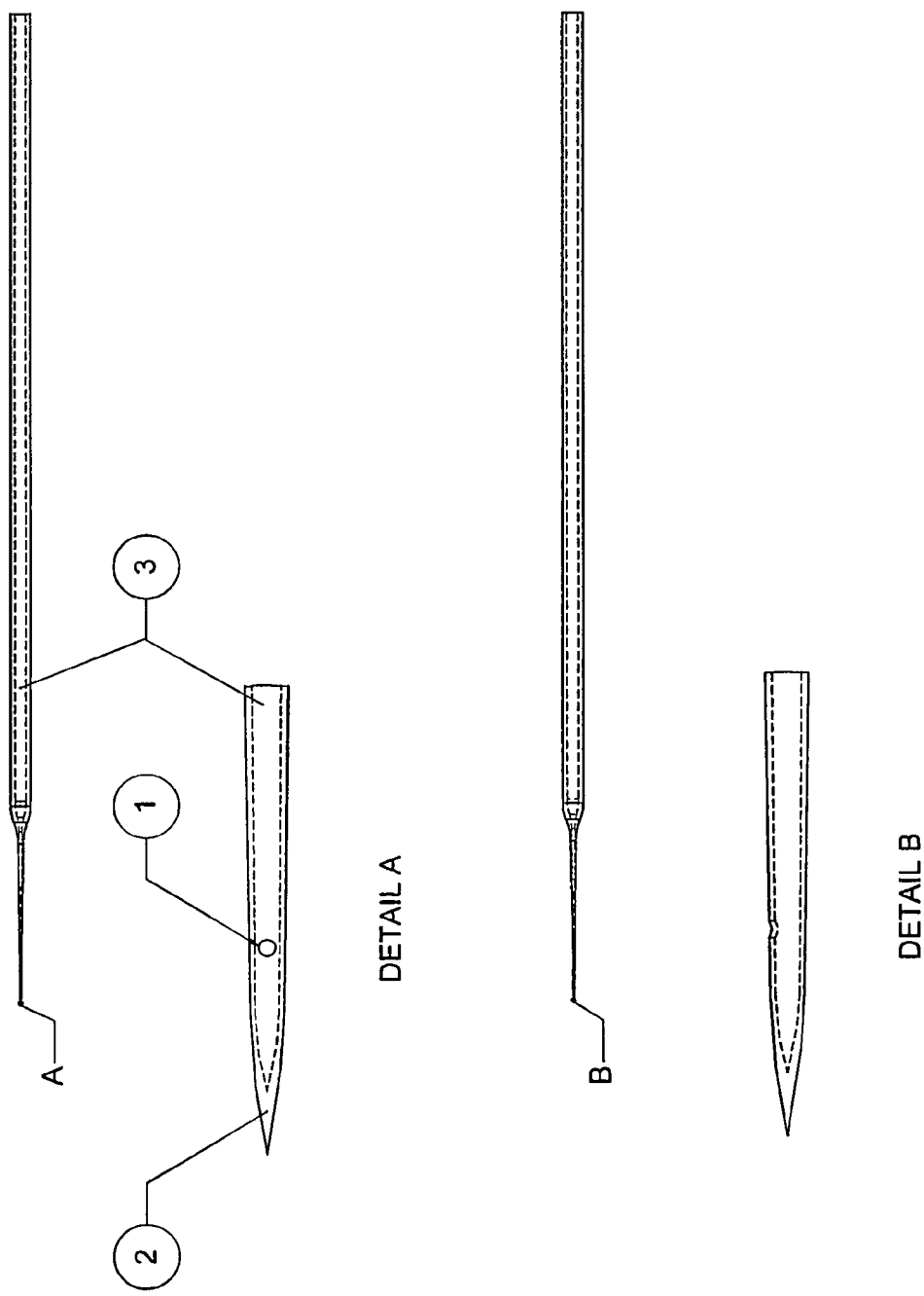
FIG. 1 is a drawing of a probe 20 microns in diameter at the location of the aperture, which is specified between 9 and 15 microns diameter.
Figure 2:
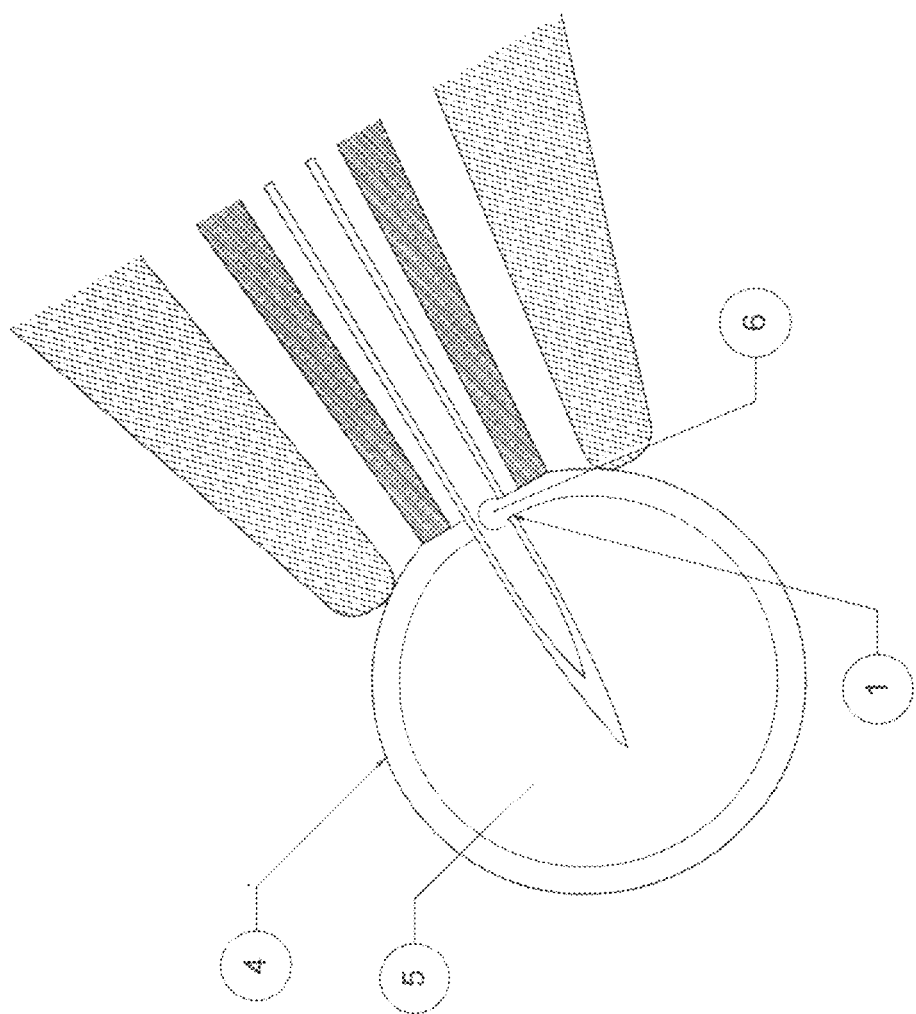
FIG. 2, is a drawing representing cellular material from the object's envelope of cells being drawn into the biopsy probe through the port.

FIG. 1.
  1. Aperture.
  2. Sealed distal tip.
  3. Pipette's hollow center.
FIG. 2.
  4. Envelope of cells.
  5. Blastocoel fluid.
  6. Biopsy sample.

DETAILED DESCRIPTION OF AN EMBODIMENT

Elements

A device for performing biopsies on a vesicular object is shown in FIGS. 1. and 2. In this embodiment the device includes a hollow pipette with a sealed tip at its distal end. Such pipette having an aperture (1) through the pipette wall (biopsy port) located only a few microns, typically 40 to 70 um, proximally from the sealed pipette's distal tip. (2). More specifically, the biopsy port is located on one sidewall of the pipette, at a right angle to the pipette's long axis, communicating with the pipette's hollow center and is created, as explained in more detail below, without damage to the pipette's far wall.

In the present embodiment, the diameter of the biopsy port is approximately one-half of the outside diameter of the pipette and the port is created in such a way as to leave the edges of the port sharp and capable of cutting or shearing cellular material from a target.

Such pipette, with the sealed distal tip and biopsy port, being referred to herein as a biopsy probe.

Method of Manufacture

A standard method of manufacture for the biopsy probe is first pulling a standard or thin-wall 1.5 mm OD (outside diameter) glass tube to a long taper, then scoring and breaking the thin glass tip at the desired diameter. This diameter has been, to date, typically between 8 um and 25 um OD. Then, on a microforge at relatively low temperature, just hot enough to melt the glass, the tip end is touched to the molten glass bead, which seals it and draws the molten tip into a sharp spike.

The aperture, or biopsy port, on the formed probe is then drilled from the side using an appropriate device, for example only, a femtosecond laser. The laser must be tuned to make a clean hole of the desired diameter through only the near sidewall of the glass tube, without damage to the inside of the far sidewall. The position of the port is determined by the diameter of the probe near the tip. For example only, if the diameter is "x", the port diameter is "0.5x" and the port is positioned "5x" to "7x" back from the sharp, and sealed, distal tip. This allows the biopsy port to be positioned (for use on an early embryo for example) at the level of the envelope of living cells when the sharp tip end is still inside the blastocoel space. The intended use of the probe, e.g. type and stage of development of an embryo to be biopsied and physical size of the cells to be captured, determines the specific position and size of the biopsy port.

Operation

A standard operation of the probe would include the following steps. The target is captured and held and the sharp and sealed distal tip of the biopsy probe is advanced, possibly as described in application Ser. No. 13/374,195. After penetrating a specific area of the object's surface, the biopsy probe's sealed distal tip (2) is advanced into the central space of the target (5) until the biopsy port (1) is aligned with the hole in the surface of the target made by the biopsy probe's sealed distal tip, or aligned in close proximity to the material to be removed from the interior of the object. A vacuum is then applied inside the biopsy probe and material is drawn into the biopsy probe through the port. (6) As the biopsy probe is withdrawn from the object, if the material is connected to the object, the material in the biopsy port is sheared, cut, or torn, away from the object leaving the object undamaged.

While the above description contains many specificities, these should not be construed as limitations on the scope of any embodiment, but as examples of various embodiments thereof. Many other ramifications and variations are possible within the teachings of the various embodiments without departing from the scope of the method and device disclosed above.

Thus the scope should be determined by the appended claims and their legal equivalents, and not by the examples given.

I claim:

1. A method for removing material from a vesicular object by:
   a) securing the object in such a manner as to allow a pipette to penetrate the object without damaging the object;
   b) such pipette:
      i) being a hollow cannula;
      ii) having a sealed distal tip capable of penetrating the object;
      iii) having one aperture located in the side of the pipette near the sealed distal tip, the aperture being created in such a manner as to leave the aperture edges sharp and capable of cutting, or otherwise removing, material from the object; and
      iv) being capable of aspiration of material from the object through the aperture via vacuum inside the pipette;
   c) advancing said pipette into the object in such a manner as to place the aperture directly adjacent to the material to be removed from the object;
   d) applying vacuum inside the pipette thereby drawing the material to be removed from the object into the pipette;
   e) removing the pipette from the object, and in those instances where the material to be removed is attached in any manner to the object, removing the pipette in such a manner as to cut or otherwise separate the material in the pipette from the object;

thereby leaving the material removed from the object inside the pipette while leaving the object undamaged.

* * * * *